United States Patent [19]

Mera et al.

[11] Patent Number: 5,750,524
[45] Date of Patent: May 12, 1998

[54] REMEDY FOR HYPERLIPIDEMIA

[75] Inventors: Yukinori Mera; Naoki Nishi; Tadashi Kurimoto; Hiroki Sato, all of Konan-machi, Japan

[73] Assignee: Zeria Pharmaceutical Co., Ltd., Tokyo, Japan

[21] Appl. No.: 793,102

[22] PCT Filed: Jul. 26, 1995

[86] PCT No.: PCT/JP95/01486

§ 371 Date: Feb. 24, 1997

§ 102(e) Date: Feb. 24, 1997

[87] PCT Pub. No.: WO96/05820

PCT Pub. Date: Feb. 29, 1996

[30] Foreign Application Priority Data

Aug. 25, 1994 [JP] Japan ................. 6-222736

[51] Int. Cl.$^6$ ............. A61K 31/50; A61K 31/495; A61K 31/415; A61K 31/38; A61K 31/16
[52] U.S. Cl. ............ 514/247; 514/252; 514/404; 514/444; 514/445; 514/608; 514/824
[58] Field of Search ................... 514/247, 252, 514/404, 444, 445, 608, 824

[56] References Cited

PUBLICATIONS

CA 118:191362, Yoshida et al., 1992.

*Primary Examiner*—Kimberly Jordan
*Attorney, Agent, or Firm*—Oblon, Spivak, McClelland, Maier & Neustadt, P.C.

[57] ABSTRACT

The invention relates to a remedy for hyperlipidemia, which comprises, as an active ingredient, an indane derivative represented by the general formula (1):

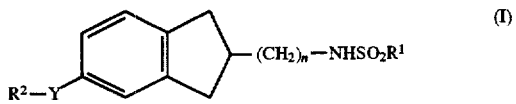

wherein $R^1$ means an alkyl group having 1–12 carbon atoms, a benzyl group, a styryl group, a naphthyl group, a phenyl group which may be substituted, or a thienyl group which may be substituted. $R^2$ denotes a carboxyl group, an alkoxycarbonyl group having 1–4 carbon atoms.

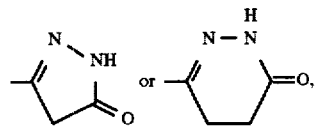

Y is a group represented by —$(CH_2)_p$— (p stands for an integer of 0–5), a group represented by —CO—$(CH_2)_q$– or —CH(OH)—$(CH_2)_q$– (q stands for an integer of 1–4, and ~ means bonding to $R^2$), an oxymethylene group, or a vinylene group, and n stands for an integer of 1–4, or a pharmaceutically acceptable salt thereof, to use of this compound for the preparation of a remedy for hyperlipidemia, and to a method for treating hyperlipidemia by making good use of this compound.

5 Claims, No Drawings

REMEDY FOR HYPERLIPIDEMIA

This application is a 371 of PCT/JP95/01486, filed Jul. 26, 1995.

TECHNICAL FIELD

The present invention relates to a remedy for hyperlipidemia, and more particularly to a remedy for hyperlipidemia, which reduces both cholesterol and triglycerides.

BACKGROUND ART

Hyperlipidemia is a morbid state in which lipids (cholesterol and triglycerides) in plasma increase, and the object of treatment for the hyperlipidemia is to prevent arteriosclerotic diseases such as myocardial infarction, cerebral infarction, occlusion of peripheral artery and arteriosclerosis.

In the past, clofibrate type medicines and HMG-CoA reducdase inhibitors have been clinically used for the prevention of and treatment for the hyperlipidemia. However, they cannot be always said to be satisfactory from the viewpoint of the prevention of and treatment for the arteriosclerotic diseases.

DISCLOSURE OF THE INVENTION

The present inventors have carried out various investigations with a view toward solving the above problems. As a result, it has been found that some indane derivatives have an effect of reducing lipids in blood, thus leading to completion of the present invention.

According to the present invention, there is thus provided a remedy for hyperlipidemia, comprising, as an active ingredient, an indane derivative represented by the following general formula (1):

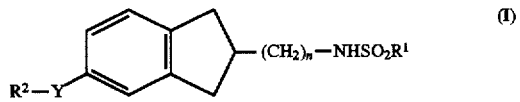

wherein $R^1$ means an alkyl group having 1–12 carbon atoms, a benzyl group, a styryl group, a naphthyl group, a phenyl group which may be substituted, or a thienyl group which may be substituted, $R^2$ denotes a carboxyl group, an alkoxycarbonyl group having 1–4 carbon atoms,

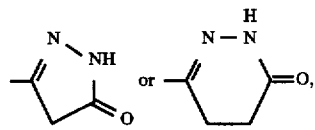

Y is a group represented by $-CH_2)_p-$ (p stands for an integer of 0–5), a group represented by $-CO-CH_2)_q-$ or $-CH(OH)-CH_2)_q-$ (q stands for an integer of 1–4, and ~ means bonding to $R^2$), an oxymethylene group, or a vinylene group, and n stands for an integer of 1–4, or a pharmaceutically acceptable salt thereof.

According to the present invention, there is also provided use of the indane derivative (1) or the pharmaceutically acceptable salt thereof for the preparation of a remedy for hyperlipidemia.

According to the present invention, there is further provided a method for treating hyperlipidemia, which comprises administering an effective amount of the indane derivative (1) or the pharmaceutically acceptable salt thereof to a patient of hyperlipidemia.

BEST MODE FOR CARRYING OUT THE INVENTION

The indane derivative [hereinafter referred to as "the compound (1)"] represented by the general formula (1), which is an active ingredient of the remedy for hyperlipidemia, is a known compound disclosed in International Publication No. WO92/15558 and is known to strongly antagonize the effect of thromboxane $A_2$ and have an effect of inhibiting platelet agglutination, but is not known to have an effect of reducing lipids in blood.

In the general formula (1), examples of "the phenyl group which may be substituted" include phenyl groups substituted by one or two alkyl groups having 1–8 carbon atoms, alkoxy groups having 1–4 carbon atoms, trifluoromethyl groups, trifluoromethoxy groups, nitro groups, amino groups, nitrile groups or halogen atoms, and a phenyl group having no substituent. Examples of "the thienyl group which may be substituted" include thienyl groups substituted by one or two alkyl groups having 1–8 carbon atoms, alkoxy groups having 1–4 carbon atoms, phenylsulfonyl groups, halogen atoms or trifluoromethyl groups, and a thienyl group having no substituent.

$R^1$ is preferably a benzyl group, a styryl group, a naphthyl group, a phenyl group which may be substituted, or a thienyl group which may be substituted. Of these, the phenyl group which may have a substituent is more preferred, with the phenyl group substituted by one or two halogen atoms being particularly preferred.

Examples of $R^2$ include a carboxyl group, alkoxycarbonyl groups having 1–4 carbon atoms, a 3-oxo-2,3,4-trihydropyrazol-5-yl group and a 3-oxo-2,3,4,5-tetrahydropyridazin-6-yl. Of these, the carboxy group is particularly preferred.

Y represents $-CH_2)_p-$ (p stands for an integer of 0–5), $-CO-CH_2)_q-$, $-CH(OH)-CH_2)_q-$ (q stands for an integer of 1–4), an oxymethylene group or a vinylene group. Of these $-CH_2)_q-$ and the oxymethylene group ($-OCH_2-$) are more preferred, with $-CH_2)_q-$ being particularly preferred.

In the compound (1), there are two kinds of optical isomers based on an asymmetric carbon atom situated at the 2-position of the indane skeleton, and a mixture thereof. All of the individual optical isomers and the mixture thereof may be used in the present invention.

The compound (1) may be used for the purposes of the present invention in the form of either an free acid or a salt thereof. When the salt is used for the purpose of the present invention, it may preferably be a pharmaceutically acceptable salt, for example, an inorganic salt such as the sodium salt, potassium salt, calcium salt or magnesium salt, or an organic salt such as the ammonium salt, pyridine salt, triethylamine salt, ethanolamine salt or basic amino acid salt. The compound (1) may be used in the form of a solvate such as a hydrate.

The compound (1) can be prepared in accordance with the process described in International Publication No. WO92/15558.

Since the compound (1) used in the present invention has an excellent effect for reducing lipids (cholesterol and triglycerides) in blood as described below, it is useful as a remedy for hyperlipidemia and can be used in treating or preventing the hyperlipidemia or other various diseases caused by the hyperlipidemia, such as myocardial infarction, cerebral infarction, occlusion of peripheral artery and arteriosclerosis.

The compound (1) or the pharmaceutically acceptable salt thereof can be orally or parenterally administered together with a pharmaceutically acceptable carrier. As preparation forms for the oral administration, the compound (1) may be provided in the form of solid preparations such as tablets, powders and capsules by suitably combining the compound (1) with proper additives, such as excipients such as lactose, mannite, corn starch and crystalline cellulose, binders such as cellulose derivatives, gum arabic and gelatin, disintegrators such as calcium carboxymethyl cellulose, and lubricants such as talc and magnesium stearate. Besides, it may also be provided in the form of liquid preparations such as solutions, suspensions and emulsions.

As preparation forms for the parenteral administration, the compound (1) may be provided in the form of injections by combining it with, for example, water, ethanol, glycerol or the like.

The dose of the compound (1) or the pharmaceutically acceptable salt thereof required to treat hyperlipidemia varies according to the preparation form and dosage form thereof, and the age and diseased condition of a patient to be dosed. However, it is generally 1–1,000 mg, preferably 5–500 mg per day for an adult. As an administration method, it is preferable to dose this amount of the compound (1) in 2 or 3 portions a day.

EXAMPLES

The present invention will hereinafter be described specifically by the following Examples. However, the present invention is not limited to these examples.

Referential Examples 1–4 will be first described as preparation examples of intermediates useful for preparation of the compounds (1), and Preparation Examples of the compounds (1) will be described subsequently.

Referential Example 1

2-[(4-Chlorophenyl)sulfonylaminomethyl]indane
Step 1: 2-(Benzyloxycarbonylaminomethyl)indane Dissolved in 150 ml of toluene were 17.6 g (0.10 mol) of 2-(indan-2-yl)acetic acid, and 15.3 ml (0.11 mol) of triethylamine and 33.0 g (0.12 mol) of diphenylphosphoryl azide were added to the solution. After the mixture was stirred at room temperature for 30 minutes, 16.6 g (0.15 mol) of benzyl alcohol were added, and the resultant mixture was refluxed for 18 hours. After cooling the mixture, the solvent was distilled off under reduced pressure, and the residue was dissolved in 500 ml of ethyl acetate, washed with 1N sodium hydroxide and then concentrated. The resultant residue was purified by column chromatography on silica gel (ethyl acetate:hexane=1:3), and the resultant crystal was recrystallized from a mixed solvent of ethyl acetate and hexane to obtain 24.3 g of 2-(benzyloxycarbonylamino-methyl)indane as a colorless needle crystal. Yield: 86%.

Melting point: 87°–89° C.
IR (KBr) cm$^{-1}$: 3325, 1675, 1525.
MS (m/z): 281 (M$^+$).

Step 2: 2-[(4-Chlorophenyl)sulfonylaminomethyl]indane

Dissolved in 100 ml of methanol were 10.6 g (37.7 mmol) of 2-(benzyloxycarbonylaminomethyl)indane, and 1.3 g of 10% palladium-carbon were added to the solution. The mixture was stirred for 4 hours under a hydrogen atmosphere. After separating the catalyst by filtration, the solvent was distilled off to obtain 5.04 g of 2-(aminomethyl)indane. This compound was immediately dissolved in 150 ml of methylene chloride, and 100 ml of water and 6.2 g of potassium carbonate were added to the solution, followed by vigorous stirring of the resultant mixture. While chilling with ice water, 8.02 g (38.0 mmol) of 4-chlorobenzenesulfonyl chloride were added in small portions. Thereafter, the mixture was stirred for 30 minutes. After an organic layer separated was taken out and dried, the solvent was distilled out of the organic layer. The resultant crystalline residue was recrystallized from a mixed solvent of ethyl acetate and hexane to obtain 9.82 g of 2-[(4-chlorophenyl)sulfonylaminomethyl]indane as a colorless needle crystal. Yield: 76%.

Melting point: 134°–135° C.
IR (KBr) cm$^{-1}$: 3250, 1315, 1150.
MS (m/z): 321 (M$^+$).

Referential Example 2

2-[3-(4-Chlorophenyl)sulfonylaminopropyl)indane
Step 1: 2-(Indan-2-yl)ethanol

Suspended in 100 ml of tetrahydrofuran were 1.02 g (26.8 mmol) of lithium aluminum hydride, and a solution of 5.06 g (26.6 mmol) of methyl (indan-2-yl)acetate in 10 ml of tetrahydrofuran was added dropwise to the suspension while chilling with ice water. After the addition, the mixture was stirred for 1 hour, and 1 ml of water, 1 ml of 15% sodium hydroxide and 3 ml of water were successively added dropwise to the mixture to decompose excess of the reducing agent. Solids were separated by filtration, the filtrate was concentrated, and the residue was purified by column chromatography on silica gel (ethyl acetate:hexane=1:4), thereby obtaining 4.30 g of a colorless oily substance. Yield: 100%.

IR (neat) cm$^{-1}$: 3320, 2920, 1480, 1050.
MS (m/z): 162 (M$^+$).

Step 2: (Indan-2-yl)acetaldehyde

Suspended in 220 ml of methylene chloride were 18.5 g (85.8 mmol) of pyridinium chlorochromate and 70 g of Celite (No. 545). While chilling with ice water, a solution of 4.30 g (26.6 mmol) of 2-(indan-2-yl)ethanol in 15 ml of methylene chloride was added dropwise to the suspension. After stirring the mixture for 1 hour while chilling with ice water, it was further stirred at room temperature for 2 hours. The reaction product was added with 250 ml of ether to dilute it. The diluted reaction product was passed through 100 g of silica gel layer to remove inorganic matter. The solvent was distilled off to obtain 3.97 g of (indan-2-yl) acetaldehyde as a colorless oily substance. Yield: 93%.

IR (neat) cm$^{-1}$: 1720, 1615, 1580.
MS (m/z): 160 (M$^+$).

Step 3: Benzyl-4-(indan-2-yl)-2-butenoate

Dissolved in 50 ml of methylene chloride were 3.97 g (24.8 mmol) of (indan-2-yl)acetaldehyde, and 12.2 g (29.8 mmol) of benzyloxycarbonylmethylene triphenylphosphorane were added to the solution, followed by stirring for 1.5 hours. After the solvent was distilled off, the residue was purified by column chromatography on silica gel (ethyl acetate:hexane=1:20) to obtain 6.45 g of a colorless oily substance. Yield: 89%.

IR (neat) cm$^{-1}$: 1715, 1650.
MS (m/z): 292 (M$^+$).

Step 4: 4-(Indan-2-yl)butanoic Acid

Dissovled in 120 ml of methanol were 6.45 g (22.1 mmol) of benzyl-4-(indan-2-yl)-2-butenoate, and 0.6 g of 10% palladium-carbon was added to the solution, followed by vigorous stirring for 2.5 hours under a hydrogen atmosphere. The catalyst was separated by filtration, and the filtrate was concentrated to obtain 3.84 g of 4-(indan-2-yl)butanoic acid as a crystal. Yield: 85%.

Melting point: 75° C.
MS (m/z): 204 (M⁺).

Step 5: 2-[3-(4-Chlorophenyl)sulfonylaminopropyl]indane

The title compound was synthesized in accordance with the step 2 of Referential Example 1, and the resultant product was recrystallized from a mixed solvent of ethyl acetate and hexane. Yield: 68%.

Melting point: 103°–104° C.
IR (nujol) cm⁻¹: 3250, 1615, 1575.
MS (m/z): 349 (M⁺).

Referential Example 3

2-[2-(4-Chlorophenyl)sulfonylaminoethyl]indane

Step 1: Preparation of (indan-2-yl)acetamide

Dissolved in 350 ml of methylene chloride were 35.3 g (0.20 mol) of (indan-2-yl)acetic acid, and 26.5 g (0.22 mol) of thionyl chloride were added to the solution. After the mixture was stirred at room temperature for 4 hours, it was refluxed further for 1.5 hours. After cooling the mixture, the resultant product was concentrated under reduced pressure. The resultant oily residue was dissolved in 100 ml of ethyl acetate, and the solution was added dropwise to 200 ml of concentrated aqueous ammonia while vigorously stirring under chilling with ice water. After stirring for 20 minutes, solids deposited were collected by filtration and recrystallized from a mixed solvent of ethyl acetate and ethanol, thereby obtaining 32.1 g of a colorless crystal. Yield: 95%.

Melting point: 152°–154° C.
IR (KBr) cm⁻¹: 3340, 3160, 1665, 1625.
MS (m/z): 175 (M⁺).

Step 2: 2-(Indan-2-yl)ethylamine

Suspended in 400 ml of tetrahydrofuran were 8.77 g (0.23 mol) of lithium aluminum hydride, and a suspension of 27.8 g (0.160 mol) of (indan-2-yl)acetamide in 100 ml of tetrahydro-furan was added under chilling with ice water. After stirring for 30 minutes at room temperature, the suspension mixture was refluxed for 5 hours. While chilling with ice water, 9 ml of water, 9 ml of 15% sodium hydroxide and 26 ml of water were added dropwise in that order to decompose excess of the reagents. Solids were separated by filtration, and the filtrate was concentrated, thereby obtaining 26.1 g of an oily substance. Yield: 100%.

IR (neat): 3360, 3280, 1600, 1585.
MS (m/z): 161 (M⁺).

Step 3: 2-[2-(4-Chlorophenyl)sulfonylaminoethyl]indane

After following the step 2 of Referential Example 1, the resultant product was recrystallized from a mixed solvent of ethyl acetate and isopropyl ether. Yield: 83%.

Melting point: 118°–121° C.
IR (KBr) cm⁻¹: 3300, 1320, 1155.
MS (m/z): 335 (M⁺).

Referential Example 4

2-[4-(4-Chlorophenyl)sulfonylaminobutyl]-indane

The title compound was obtained from 4-(indan-2-yl) butanoic acid in accordance with the process of Referential Example 3.

Melting point: 77° C.
IR (KBr) cm⁻¹: 3260, 1150.
MS (m/z): 363 (M⁺).

Preparation Example 1

[2-(Phenylsulfonylaminomethyl)indan-5-yl]acetic Acid

Step 1: [5-(Ethoxycarbonylmethyl)indan-2-yl]acetic Acid

Dissolved in 100 ml of dichloroethane were 17.6 g (0.10 mol) of (indan-2-yl)acetic acid and 16.9 g (0.10 mol) of ethyl-α-chloro-α-(methylthio)acetate. While chilling with ice water, 17.6 ml (0.15 mol) of stannic chloride were added dropwise to the solution. The mixture was stirred at room temperature for 40 minutes, and the reaction mixture was poured into ice water. The resultant organic layer was washed with water, dried and then concentrated. The residue was dissolved in 250 ml of acetic acid, and 70 g of zinc powder were added, followed by heating at 110° C. for 1 hour. After cooling the mixture, solids were separated by filtration, and the filtrate was concentrated under reduced pressure. After the residue was added with 500 ml of chloroform, washed with water and dried, the solvent was distilled off to obtain 24.1 g of a colorless solid. Yield: 92%.

Melting point: 56°–57° C.
IR (KBr) cm⁻¹: 2990, 2910, 1725, 1680.
MS (m/z): 262 (M⁺).

Step 2: Ethyl [2-(benzyloxycarbonylaminomethyl)indan-5-yl]acetate

Dissolved in 140 ml of toluene were 11.2 g (42.8 mmol) of [5-(ethoxycarbonylmethyl)indan-2-yl]acetic acid and 6.5 ml (46.7 mmol) of triethylamine, and 14.1 g (51.4 mmol) of diphenylphosphoryl azide were added to the solution. After the mixture was then stirred at room temperature for 30 minutes, 5.05 g (46.7 mmol) of benzyl alcohol were added. The resultant mixture was refluxed for 14 hours. After cooling, the reaction mixture was washed successively with 1N hydrochloric acid, water and 1N sodium hydroxide and then dried. After distilling off the solvent, the residue was purified by column chromatography on silica gel (chloroform) to obtain 12.7 g of a colorless solid. Yield: 81%.

Melting point: 38°–41° C.
IR (KBr) cm⁻¹: 1725, 1675.
MS (m/z): 367 (M⁺).

Step 3: Ethyl [2-(phenylsulfonylaminomethyl)indan-5-yl]acetate

Dissolved in 30 ml of methanol were 1.80 g (4.90 mmol) of ethyl [2-(benzyloxycarbonylaminomethyl)indan-5-yl]acetate, and 500 mg of 10% palladium-carbon were added to the solution, followed by stirring for 2 hours under a hydrogen atmosphere. The catalyst was separated by filtration, and the filtrate was concentrated. The resultant residue was dissolved in 15 ml of ethyl acetate, and 10 ml of water and 1.18 g (8.51 mmol) of potassium carbonate were added to the solution. While vigorously stirring, 902 mg (5.11 mmol) of benzenesulfonyl chloride were then added dropwise. After the addition, the mixture was stirred for 1 hour, and an organic layer separated was taken out, dried and then concentrated under reduced pressure. The residue was purified by column chromatography on silica gel (chloroform) to obtain 1.78 g of a colorless oily substance. Yield: 97%.

IR (nujol): 1725, 1615, 1580.
MS (m/z): 373 (M⁺).

Step 4: [2-(Phenylsulfonylaminomethyl)-indan-5-yl]acetic Acid

Dissolved in 3 ml of methanol were 844 mg (2.26 mmol) of ethyl [2-(phenylsulfonylaminomethyl)indan-5-yl]acetate, and 5 ml of 1N sodium hydroxide were added to the solution, followed by stirring at room temperature for 1 hour. After distilling off methanol, the resultant aqueous layer was washed with chloroform, and 1N hydrochloric acid was added to acidify the aqueous layer. Solids deposited were extracted with ethyl acetate, and the resultant extract was dried and then concentrated. The residue was recrystallized from ethyl acetate to obtain 679 mg of a crystal. Yield: 87%.

Melting point: 140°–141° C.
IR (KBr) cm⁻¹: 3305, 2950, 1695.
MS (m/z): 345 (M⁺).

The following compounds of Preparation Examples 2–22 were synthesized in accordance with the preparation process described above.

Incidentally, the solvents used for recrystallization are shown in parentheses following the melting point.

Preparation Example 2

[2-[(4-Methylphenyl)sulfonylaminomethyl]-indan-5-yl]acetic Acid

Melting point: 153°–156° C. (ethanol).
IR (KBr) cm⁻¹: 3250, 2930, 1715.
MS (m/z): 359 (M⁺).

Preparation Example 3

[2-[(3,4-Dimethoxyphenyl)sulfonylaminomethyl]indan-5-yl]acetic Acid

Melting point: 132°–133° C. (ethanol).
IR (KBr) cm⁻¹: 3255, 2930, 1690.
MS (m/z): 405 (M⁺).

Preparation Example 4

[2-[(trans-2-Styryl)sulfonylaminomethyl]-indan-5-yl]acetic Acid

Melting point: 170°–172° C. (ethanol).
IR (KBr) cm⁻¹: 3260, 2930, 1695.
MS (m/z): 371 (M⁺).

Preparation Example 5

[2-(Benzylsulfonylaminomethyl)indan-5-yl]acetic Acid

Melting point: 181°–182° C. (ethanol).
IR (KBr) cm⁻¹: 3225, 2930, 1695.
MS (m/z): 359 (M⁺).

Preparation Example 6

[2-(1-Naphthylsulfonylaminomethyl)indan-5-yl]acetic Acid

Melting point: 58°–60° C.
IR (KBr) cm⁻¹: 3275, 2920, 1700.
MS (m/z): 395 (M⁺).

Preparation Example 7

[2-(2-Naphthylsulfonylaminomethyl)indan-5-yl]acetic Acid

Melting point: 180°–182° C. (ethanol).
IR (KBr) cm⁻¹: 3230, 1925, 1690.
MS (m/z): 395 (M⁺).

Preparation Example 8

[2-(2-Thienylsulfonylaminomethyl)indan-5-yl]acetic Acid

Melting point: 110°–111° C. (aqueous methanol).
IR (KBr) cm⁻¹: 3250, 2920, 1700.
MS (m/z): 351 (M⁺).

Preparation Example 9

[2-[(5-Phenylsulfonyl-2-thienyl)sulfonylaminomethyl]-indan-5-yl]acetic Acid

Melting point: 164°–166° C. (ethanol).
IR (KBr) cm⁻¹: 3260, 2920, 1695.
MS (m/z): 491 (M⁺).

Preparation Example 10

[2-[(4-Trifluoromethylphenyl)sulfonylaminomethyl]indan- 5-yl]acetic Acid

Melting point: 183°–186° C. (ethanol).
IR (KBr) cm⁻¹: 3275, 2950, 1690, 1325, 1150.
MS (m/z): 413 (M⁺).

Preparation Example 11

[2-[(2,4-Dichlorophenyl)sulfonylaminomethyl]indan-5-yl]acetic Acid

Melting point: 153°–154° C. (ethanol).
IR (KBr) cm⁻¹: 3325, 2945, 1700, 1330, 1165.
MS (m/z): 413 (M⁺).

Preparation Example 12

[2-[(4-Methoxyphenyl)sulfonylaminomethyl]indan-5-yl]acetic Acid

Melting point: 171°–173° C. (ethanol).
IR (KBr) cm⁻¹: 3280, 2950, 1695, 1320, 1155.
MS (m/z): 375 (M⁺).

Preparation Example 13

[2-[(4-Fluorophenyl)sulfonylaminomethyl]indan-5-yl]acetic Acid

Melting point: 180°–181° C. (aqueous ethanol).
IR (KBr) cm⁻¹: 3300, 1700, 1155.
MS (m/z): 363 (M⁺).

Preparation Example 14

[2-[(4-Bromophenyl)sulfonylaminomethyl]indan-5-yl]acetic Acid

Melting point: 182°–183° C. (aqueous ethanol).
IR (KBr) cm⁻¹: 3295, 2940, 1700, 1330, 1170.
MS (m/z): 423 (M⁺).

Preparation Example 15

[2-[(3,4-Dichlorophenyl)sulfonylaminomethyl]indan-5-yl]acetic Acid

Melting point: 174°–176° C. (aqueous ethanol).
IR (KBr) cm⁻¹: 3250, 1695, 1325, 1160.
MS (m/z): 415 (M⁺).

Preparation Example 16

[2-[(4-Ethylphenyl)sulfonylaminomethyl]indan-5-yl]acetic Acid

Melting point: 140°–143° C. (ethyl acetate-hexane).
IR (KBr) cm⁻¹: 3280, 1700, 1155.

MS (m/z): 373 (M⁺).

Preparation Example 17

[2-[(4-t-butylphenyl)sulfonylaminomethyl]indan-5-yl]acetic Acid

Melting point: 187°–189° C. (aqueous ethanol).
IR (KBr) cm⁻¹: 3260, 1700, 1160.
MS (m/z): 401 (M⁺).

Preparation Example 18

[2-[(4-Octylphenyl)sulfonylaminomethyl]-indan-5-yl]acetic Acid

Melting point: 136°–137° C. (aqueous ethanol).
IR (KBr) cm⁻¹: 3300, 2920, 1700, 1330, 1155.
MS (m/z): 457 (M⁺).

Preparation Example 19

[2-[(4-Trifluoromethoxyphenyl)sulfonylaminomethyl]indan-5-yl]acetic Acid

Melting point: 185°–186° C. (aqueous ethanol).
IR (KBr) cm⁻¹: 3300, 2940, 1700, 1155.
MS (m/z): 429 (M⁺).

Preparation Example 20

[2-[(4-Butoxyphenyl)sulfonylaminomethyl]indan-5-yl]acetic Acid

Melting point: 151°–152° C. (aqueous ethanol).
IR (KBr) cm⁻¹: 3270, 1690.
MS (m/z): 417 (M⁺).

Preparation Example 21

[2-[(4-Cyanophenyl)sulfonylaminomethyl]indan-5-yl]acetic Acid

Melting point: 198°–199° C. (aqueous ethanol).
IR (KBr) cm⁻¹: 3300, 2940, 1700, 1335, 1160.
MS (m/z): 370 (M⁺).

Preparation Example 22

[2-[(4-Nitrophenyl)sulfonylaminomethyl]indan-5-yl]acetic Acid

Melting point: 148°–149° C. (aqueous ethanol).
IR (KBr) cm⁻¹: 3240, 1705, 1350, 1155.
MS (m/z): 390 (M⁺).

Preparation Example 23

[2-[(4-Aminophenyl)sulfonylaminomethyl]indan-5-yl]acetic Acid

Dissolved in 50 ml of methanol were 1.95 g of [2-[(4-nitrophenyl)sulfonylaminomethyl]indan-5-yl]acetic acid obtained in Preparation Example 22, and 200 mg of 10% palladium-carbon were added to the solution, followed by stirring for 2 hours under a hydrogen atmosphere. After the catalyst was separated by filtration, and the filtrate was concentrated, the resultant residue was recrystallized from ethanol to obtain 1.43 g of a crystal. Yield: 79%.

Melting point: 201°–202° C.
IR (KBr) cm⁻¹: 3470, 3380, 3280, 1695, 1150.
MS (m/z): 360 (M⁺).

Preparation Example 24

[2-[(4-Chlorophenyl)sulfonylaminomethyl]indan-5-yl]acetic Acid

Step 1: Preparation of Ethyl [2-[(4-chlorophenyl)sulfonylamino-methyl]indan-5-yl]acetate Dissolved in 50 ml of methylene chloride were 16.1 g (50 mmol) of 2-[(4-chlorophenyl)sulfonylaminomethyl]indane prepared in Referential Example 1 and 9.27 g (55.0 mmol) of ethyl α-chloro-α-(methylthio)acetate, and 6.44 ml (55.0 mmol) of stannic chloride were slowly added dropwise to the solution. After the mixture was stirred for 3 hours, the liquid reaction mixture was poured into ice water. An organic layer separated was taken out, washed with water, dried and then concentrated. The residue was dissolved in 180 ml of acetic acid, and 40 g of zinc powder were added, followed by heating at 110° C. for 1 hour. After cooling, solids were separated by filtration, and the filtrate was fully washed with chloroform, and the solvent was then distilled off. The residue was dissolved in 300 ml of ethyl acetate, and the solution was washed with water, a saturated aqueous solution of sodium bicarbonate and water in that order, and dried. The solvent was distilled off under reduced pressure, and the residue was recrystallized from a mixed solvent of ethyl acetate and hexane, thereby obtaining 16.7 g of a colorless needle crystal. Yield: 82%.

Melting point: 94°–96° C.
IR (KBr) cm⁻¹: 3230, 1730.
MS (m/z): 379 (M⁺).

Step 2: [2-[(4-Chlorophenyl)sulfonylaminomethyl]indan-5-yl]acetic Acid

Suspended in 50 ml of 1N sodium hydroxide were 16.5 g of ethyl [2-[(4-chlorophenyl)sulfonylaminomethyl]indan-5-yl]-acetate, and the suspension was heated at 80° C. for 1 hour. After cooling, hydrochloric acid was added to the suspension to acidify it. A crystal deposited was collected by filtration. The crystal was recrystallized from 80% ethanol to obtain 14.0 g of the title compound as a colorless needle crystal. Yield: 91%.

Melting point: 182°–186° C.
IR (KBr) cm⁻¹: 3340, 1700.
MS (m/z): 379 (M⁺).

Incidentally, 2.65 g (7.00 mmol) of [2-[(4-chlorophenyl)sulfonylaminomethyl]indan-5-yl]acetic acid thus obtained were dissolved in 15 ml of 1N sodium hydroxide, and the solution was then passed through 100 ml of polystyrene gel (HP-20). Elution was conducted with 80% methanol, and the resultant eluate was concentrated to obtain 2.39 g of sodium [2-[(4-chlorophenyl)sulfonylaminomethyl]indan-5-yl]acetate as a colorless crystal. The crystal was recrystallized from 95% ethanol, thereby obtaining 2.39 g of a colorless prismatic crystal. Yield: 85%.

Melting point (decomposition point): 258°–261° C.

The following compounds of Preparation Examples 25–28 were obtained in accordance with the preparation process used in Preparation Example 24.

Preparation Example 25

[2-(2-Phenylsulfonylaminoethyl)indan-5-yl]acetic Acid

Melting point: 102°–103° C. (ethyl acetate-hexane).
IR (nujol) cm⁻³: 3240, 1695.

MS (m/z): 359 (M⁺).

Preparation Example 26

[2-[2-(4-Chlorophenyl)sulfonylaminoethyl]indan-5-yl]acetic Acid

Melting point: 146°–147° C. (ethyl acetate-hexane).
IR (nujol) cm⁻¹: 3330, 1705.
MS (m/z): 393 (M⁺).

Preparation Example 27

[2-[3-(4-Chlorophenyl)sulfonylaminopropyl]indan-5-yl]acetic Acid

Melting point: 163°–164° C. (aqueous ethanol).
IR (KBr) cm⁻¹: 3260, 1690.
MS (m/z): 407 (M⁺).

Preparation Example 28

[2-[4-(4-Chlorophenyl)sulfonylaminobutyl]indan-5-yl]acetic Acid

Melting point: 126° C. (aqueous ethanol).
IR (KBr) cm⁻¹: 3280, 1700.
MS (m/z): 421 (M⁺).

Preparation Example 29

2-(Phenylsulfonylaminomethyl)indane-5-oxyacetic Acid

Step 1: Methyl (5-acetylindan-2-yl)acetate

Added to 160 ml of methylene chloride were 52.9 g (0.388 mol) of anhydrous aluminum chloride. While chilling with ice water, a solution of 25.03 g (0.132 mol) of methyl (indan-2-yl)acetate in 40 ml of methylene chloride was added dropwise to the solution, followed by the addition of 13.1 ml (0.185 mol) of acetyl chloride. After stirring the mixture at the same temperature for 40 minutes, the reaction mixture was poured into ice water to take out an organic layer separated. After the organic layer was washed with water and dried, the solvent was distilled off under reduced pressure. The resultant residue was purified by column chromatography on silica gel (ethyl acetate-hexane=1:2), thereby obtaining 27.8 g of an oily substance. Yield: 91%.
IR (neat) cm⁻¹: 1725, 1690.
MS (m/z): 232 (M⁺).

Step 2: Methyl (5-actoxyindan-2-yl)acetate

Dissolved in 200 ml of methylene chloride were 11.0 g (47.0 mmol) of methyl (5-acetylindan-2-yl]acetate, and 14.6 g (67 mmol) of m-chloroperbenzoic acid were added to the solution. The mixture was stirred at room temperature for 4 hours and then refluxed for 17 hours. The reaction mixture was washed successively with a saturated aqueous solution of sodium hydrogencarbonate and water and dried. The solvent was distilled off, and the resultant residue was purified by column chromatography on silica gel (chloroform) to obtain 11.3 g of an oily substance. Yield: 97%.
IR (neat) cm⁻¹: 1750, 1730.
MS (m/z): 248 (M⁺).

Step 3: (5-Benzyloxyindan-2-yl)acetic Acid

Dissolved in 150 ml of methanol were 9.62 g (38.8 mmol) of methyl (5-acetoxyindan-2-yl)acetate, and 1.17 g (8.5 mmol) of potassium carbonate were added, followed by stirring at room temperature for 1 hour. The solvent was distilled off under reduced pressure, and the residue was dissolved in 150 ml of acetone. Added to the solution were 5.98 g (43.0 mmol) of potassium carbonate and 7.27 g (42.5 mmol) of benzyl bromide, and the mixture was refluxed for 5 hours. After cooling, solids were separated by filtration, and the filtrate was concentrated under reduced pressure. The residue was dissolved in 100 ml of methanol, and 12 ml of 20% sodium hydroxide was added to the solution, followed by heating at 50° C. for 1 hour. After cooling, methanol was distilled off, and the residue was acidified with concentrated hydrochloric acid. Thereafter, solids deposited were extracted with chloroform. The resultant organic layer was washed with water, dried and then concentrated under reduced pressure, thereby obtaining a pale brown solid. The solid was recrystallized from a mixed solvent of isopropyl ether and ethyl acetate to obtain 5.97 g of a colorless crystal. Yield: 68%.
Melting point: 127°–129° C.
IR (KBr) cm⁻¹: 1695, 1615, 1485.
MS (m/z): 282 (M⁺).

Step 4: 5-Benzyloxy-2-(t-butoxycarbonylaminomethyl) indan

Dissolved in 120 ml of t-butanol were 4.27 g (15.0 mmol) of (5-benzyloxyindan-2-yl)acetic acid, and 1.96 g (19.4 mmol) of triethylamine and 5.03 g (18.3 mmol) of diphenylphosphoryl azide were successively added to the solution, followed by reflux for 27 hours. After cooling, the reaction mixture was concentrated under reduced pressure, and the residue was dissolved in 200 ml of ethyl acetate. After the solution was washed successively with 1N hydrochloric acid, water, 1N sodium hydroxide and water, the solvent was distilled off. The residue was purified by column chromatography on silica gel (chloroform), and the purified product was recrystallized from ethyl acetate and isopropyl ether, thereby obtaining 4.71 g of a colorless crystal. Yield: 89%.
Melting point: 95°–98° C.
IR (KBr) cm⁻¹: 3350, 1670.
MS (m/z): 353 (M⁺).

Step 5: 2-(t-Butoxycarbonylaminomethyl)-5-hydroxyindane

Dissolved in 100 ml of methanol were 3.53 g (10.0 mmol) of 5-benzyloxy-2-(t-butoxycarbonylaminomethyl)indane. After 0.3 g of 10% palladium-carbon was added to the solution, the mixture was stirred for 4 hours under a hydrogen atmosphere. The catalyst was separated by filtration, and the filtrate was concentrated under reduced pressure. The residue was purified by column chromatography on silica gel (ethyl acetate:hexane=1:2) to obtain 2.79 g of a colorless oily substance. Yield: 94%.
IR (neat) cm⁻¹: 3350, 1690.
MS (m/z): 263 (M⁺).

Step 6: Ethyl [2-(t-butoxycarbonylaminomethyl)indane-5-oxy]acetate

Dissolved in 20 ml of acetone were 1.85 g (6.20 mmol) of 2-(t-butoxycarbonylaminomethyl)-5-hydroxyindane, and 1.52 g (11.0 mmol) of potassium carbonate and 1.10 g (6.60 mmol) of ethyl bromoacetate were added to the solution. The mixture was refluxed for 3.5 hours. After cooling, solids were separated by filtration, and the filtrate was concentrated. The resultant residue was purified by column chromatography on silica gel (ethyl acetate:hexane=1:2) to obtain 1.90 g of a colorless crystal. Yield; 80%.
Melting point: 56°–63° C.
IR (neat) cm⁻¹: 1730, 1675.
MS (m/z): 343 (M⁺).

Step 7: Ethyl [2-(phenylsulfonylaminomethyl)indane-5-oxy]acetate

Dissolved in 6 ml of methylene chloride were 1.77 g (5.00 mmol) of ethyl [2-(t-butoxycarbonylaminomethyl)indane-5-oxy]acetate, and 4 ml of trifluoroacetic acid were added under chilling with ice water, followed by stirring for 1 hour. The liquid reaction mixture was diluted with 40 ml of methylene chloride, and a solution of 8.37 g (60 mmol) of potassium carbonate in 40 ml of water was added, followed by vigorous stirring. After 10 minutes, 1.07 g (6.00 mmol) of phenyl-sulfonyl chloride were added, and the resultant mixture was stirred further for 1.5 hours. An organic layer separated was taken out, dried and then concentrated, and the residue was purified by column chromatography on silica gel (ethyl acetate: hexane=1:1), thereby obtaining 1.68 g of a colorless oily substance. Yield: 88%.

IR (nujol) $cm^{-1}$: 3280, 1750, 1320, 1155.

MS (m/z): 389 ($M^+$).

Step 8: 2-(Phenylsulfonylaminomethyl)indane-5-oxy]acetic Acid

Dissolved in a liquid mixture of 30 ml of methanol and 6 ml of 1N sodium hydroxide were 1.67 g (4.36 mmol) of ethyl [2-(phenylsulfonylaminomethyl)indane-5-oxy]acetate, and the solution was stirred at room temperature for 1 hour. Methanol was distilled off, and concentrated hydrochloric acid was added to the residue to acidify the residue. The resultant deposit was extracted with chloroform. After the extract was concentrated, and the resultant solids were recrystallized from acetic acid and isopropyl ether, thereby obtaining 1.33 g of a colorless crystal. Yield: 86%.

Melting point: 150°–151° C.

IR (KBr) $cm^{-1}$: 3270, 1745.

MS (m/z): 361 ($M^+$).

The following compounds of Preparation Examples 30–32 were obtained in accordance with the preparation process used in Preparation Example 29.

Preparation Example 30

2-[(4-Chlorophenyl)sulfonylaminomethyl]indane-5-oxyacetic Acid

Melting point (decomposition point): 185°–188° C. (aqueous ethanol).

IR (KBr) $cm^{-1}$: 3240, 1720.

MS (m/z): 395 ($M^+$).

Preparation Example 31

2-[(4-Methoxyphenyl)sulfonylaminomethyl]indane-5-oxyacetic Acid

Melting point: 155°–156° C. (aqueous ethanol).

IR (KBr) $cm^{-1}$: 3270, 1750, 1730, 1705.

MS (m/z): 391 ($M^+$).

Preparation Example 32

2-[2-(4-Chlorophenyl)sulfonylaminoethyl]indane-5-oxyacetic Acid

Melting point: 156°–158° C. (aqueous ethanol).

IR (KBr) $cm^{-1}$: 3300, 1715.

MS (m/z): 409 ($M^+$).

Preparation Example 33

[2-[(4-Chlorophenyl)sulfonylaminomethyl]indan-5-yl]carboxylic Acid

Step 1: 5-Acethyl-2-[(4-chlorophenyl)sulfonylaminomethyl]indane

Dissolved in 5 ml of methylene chloride were 369 mg (1.15 mmol) of 2-[(4-chlorophenyl)sulfonylaminomethyl] indane prepared in Referential Example 1. While chilling with ice water, 460 mg (4.20 mmol) of anhydrous aluminum chloride were added to the solution, and 302 mg (3.80 mmol) of acetyl chloride were then added dropwise. After stirring at the same temperature for 30 minutes, the reaction mixture was poured into ice water. After the resultant organic layer was washed with water and a saturated aqueous solution of sodium bicarbonate, and dried, the solvent was distilled off. The residue was recrystallized from a mixed solvent of ethyl acetate and isopropyl ether to obtain 310 mg of a colorless crystal. Yield: 75%.

Melting point: 101°–105° C.

IR (KBr) $cm^{-1}$: 3250, 1675, 1320, 1150.

MS (m/z): 363 ($M^+$).

Step 2: [2-[(4-Chlorophenyl)sulfonylaminomethyl]indan-5-yl]carboxylic Acid

While chilling with ice salt water, 4.90 g (122 mmol) of sodium hydroxide were dissolved in 50 ml of water, and 1.6 ml (31.0 mmol) of bromine were added dropwise thereto. While chilling with ice salt water, this solution was added dropwise to a solution of 2.85 g (7.50 mmol) of 5-acetyl-2-[(4-chloro-phenyl)sulfonylaminomethyl]indane in 100 ml of 90% dioxane. Thereafter, the mixture was continuously stirred for 1 hour while raising the temperature of the mixture to room temperature. After a 10% solution of sodium thiosulfate was added to the liquid reaction mixture, and 1N hydrochloric acid was further added to acidify the mixture, the mixture was extracted with ethyl acetate. After the solvent was distilled off, the residue was recrystallized from acetic acid to obtain 2.36 g of a colorless crystal. Yield: 86%.

Melting point (decomposition point): 226°–228° C.

IR (KBr) $cm^{-1}$: 3240, 1675.

MS (m/z): 363 ($M^+$).

The following compounds of Preparation Examples 34–36 were obtained in accordance with the preparation process used in Preparation Example 33.

Preparation Example 34

[2-[2-(4-Chlorophenyl)sulfonylaminoethyl]indan-5-yl]carboxylic Acid

Melting point (decomposition point): 210°–213° C.

IR (KBr) $cm^{-1}$: 3270, 1685.

MS (m/z): 379 ($M^+$).

Preparation Example 35

[2-[3-(4-Chlorophenyl)sulfonylaminopropyl]indan-5-yl]carboxylic Acid

Melting point (decomposition point): 183°–186° C.

IR (KBr) $cm^{-1}$: 3270, 1670.

MS (m/z): 393 ($M^+$).

Preparation Example 36

[2-[4-(4-Chlorophenyl)sulfonylaminobutyl]indan-5-yl]carboxylic Acid

Melting point: 152°–154° C.

IR (KBr) $cm^{-1}$: 3280, 1685.

MS (m/z): 407 (M⁺).

Preparation Example 37 trans-3-[2-[(4-Chlorophenyl)sulfonylaminomethyl]
indan-5-yl]acrylic Acid

Step 1: 5-Formyl-2-[(4-chlorophenyl)sulfonylaminomethyl]
indane

Suspended in 20 ml of methylene chloride were 5.33 g (40.0 mmol) of anhydrous aluminum chloride, and 1.61 g (5.00 mmol) of 2-[(4-chlorophenyl)sulfonylaminomethyl] indane prepared in Referential Example 1 were added to the solution, followed by refrigeration of the mixture to −20° C. After 0.68 ml (7.5 mmol) of dichloromethyl ether was slowly added dropwise to this mixture, the resultant mixture was stirred for 1 hour at the same temperature. After the reaction mixture was poured into ice water and stirred for 1 hour, an organic layer separated was taken out, washed with water and dried. Thereafter, the solvent was distilled off. The residue was purified by column chromatography on silica gel (chloroform) and recrystallized from a mixed solvent of ethyl acetate and hexane to obtain 375 mg of a colorless crystal. Yield: 22%.

Melting point: 80°–82° C.
IR (KBr) cm⁻¹: 3240, 1685.
MS (m/z): 349 (M⁺).

Step 2: Ethyl-trans-3-[2-[(4-chlorophenyl)sulfonylaminomethyl]indan-5-yl]acrylate Added to 20 ml of methylene chloride were 1.29 g (3.68 mmol) of 5-formyl-2-[(4-chlorophenyl)sulfonylaminomethyl]indane and 1.28 g (3.68 mmol) of carboethoxymethylene triphenyl-phosphorane, and the mixture was stirred at room temperature for 16 hours. The liquid reaction mixture was purified by column chromatography on silica gel (chloroform), and the resultant solids were recrystallized from a mixed solvent of ethyl acetate and hexane, thereby obtaining 1.18 g of a colorless crystal. Yield: 77%.

Melting point: 113°–115° C.
IR (KBr) cm⁻¹: 3230, 1705, 1630.
MS (m/z): 387 (M⁺).

Step 3: trans-3-[2-[(4-Chlorophenyl)sulfonylaminomethyl] indan-5-yl]acrylic Acid Suspended in 5 ml of 2N sodium hydroxide were 465 mg (1.20 mmol) of ethyl-trans-3-[2-[(4-chlorophenyl)sulfonylaminomethyl]indan-5-yl]acrylate, and the suspension was stirred at room temperature for 5 hours. Added to the suspension was 2N hydrochloric acid to acidify the suspension, and a crystal deposited was extracted with methylene chloride. After the extract was dried, the solvent was distilled off, and the residue was recrystallized from ethanol, thereby obtaining 405 mg of a colorless crystal. Yield: 86%.

Melting point: 240°–241° C.
IR (KBr) cm⁻¹: 3260, 1685, 1630.
MS (m/z): 359 (M⁺).

Preparation Example 38

3-[2-[(4-Chlorophenyl)sulfonylaminomethyl]indan-
5-yl]propionic Acid

Step 1: Ethyl-3-[2-[(4-Chlorophenyl)sulfonylaminomethyl] indan-5-yl]propionate

Dissolved in 10 ml of ethanol were 387 mg (1.00 mmol) of ethyl-trans-3-[2-[(4-chlorophenyl)sulfonylaminomethyl] indan-5-yl]acrylate obtained in the step 2 of Preparation Example 37, and 24 mg (0.1 mmol) of nickel chloride hexahydrate were added to the solution. After 76 mg (2.00 mmol) of sodium boron hydride were added to the solution in small portions while chilling with ice water, the resultant mixture was stirred overnight at room temperature. After ethanol was distilled off, 10 ml of water were added to the residue, and the resultant product was extracted with ethyl acetate. The extract was washed with water, dried and then concentrated. The resultant crystal was recrystallized from a mixed solvent of hexane and ether to obtain 241 mg of a colorless crystal. Yield: 62%.

Melting point: 90°–93° C.
IR (KBr) cm⁻¹: 3260, 1725, 1585, 1320, 1155.
MS (m/z): 389 (M⁺).

Step 2: 3-[2-[(4-Chlorophenyl)sulfonylaminomethyl]indan-5-yl]propionic Acid

Suspended in 3 ml of 2N sodium hydroxide were 195 mg (0.50 mmol) of ethyl-3-[2-[(4-chlorophenyl)sulfonylaminomethyl]indan-5-yl]propionate, and the suspension was heated at 70° C. for 2 hours. After cooling, the suspension was acidified with concentrated hydrochloric acid under chilling with ice water. A crystal deposited was collected by filtration and recrystallized from a mixed solvent of ethyl acetate and hexane, thereby obtaining 137 mg of a colorless flaky crystal. Yield: 76%.

Melting point: 189°–191° C.
IR (KBr) cm⁻¹: 3270, 1695, 1595, 1320, 1160.
MS (m/z): 361 (M⁺).

Preparation Example 39

The following compound was obtained in the same manner as in Preparation Example 38.

3-[2-[(4-Methoxyphenyl)sulfonylaminomethyl]
indan-5-yl]propionic Acid

Melting point: 147°–151° C. (aqueous ethanol).
IR (KBr) cm⁻¹: 3260, 1695, 1155.
MS (m/z): 389 (M⁺).

Preparation Example 40

4-[2-[(4-Chlorophenyl)sulfonylaminomethyl]indan-
5-yl]-4-oxobutanoic Acid

Suspended in 35 ml of dichloroethane were 6.82 g (51.2 mmol) of anhydrous aluminum chloride, and 4.26 g (13.3 mmol) of 2-[(4-chlorophenyl)sulfonylaminomethyl]indane prepared in Referential Example 1 were added thereto. While chilling with ice water, 2.07 g (20.6 mmol) of succinic anhydride were added to this suspension in small portions. Thereafter, the mixture was stirred at room temperature for 1.5 hours, and the liquid reaction mixture was poured into ice water. A crystal deposited was collected by filtration, washed with water and then recrystallized from acetic acid to obtain 4.75 g of a colorless crystal. Yield: 85%.

Melting point (decomposition point): 192°–194° C.
IR (KBr) cm⁻¹: 3250, 1690, 1675.
MS (m/z): 421 (M⁺).

The following compounds of Preparation Examples 41–44 were obtained in accordance with the preparation process used in Preparation Example 40.

Preparation Example 41

4-[2-[2-(4-Chlorophenyl)sulfonylaminoethyl]indan-
5-yl]-4-oxobutanoic Acid

Melting point: 144°–146° C. (acetic acid).
IR (KBr) cm⁻¹: 3300, 1715, 1675.

MS (m/z): 435 (M⁺).

Preparation Example 42

4-[2-[(4-Methoxyphenyl)sulfonylaminomethyl]indan-5-yl]-4-oxobutanoic Acid

Melting point: 150°–151° C. (aqueous ethanol).
IR (KBr) cm⁻¹: 3260, 1695, 1680.
MS (m/z): 417 (M⁺).

Preparation Example 43

5-[2-[(4-Chlorophenyl)sulfonylaminomethyl]indan-5-yl]-5-oxopentanoic Acid

Melting point: 159°–161° C. (ethanol).
IR (KBr) cm⁻¹: 3260, 1690, 1680, 1155.
MS (m/z): 435 (M⁺).

Preparation Example 44

6-[2-[(4-Chlorophenyl)sulfonylaminomethyl]indan-5-yl]-6-oxohexanoic Acid

Melting point: 154°–155° C. (aqueous ethanol).
IR (KBr) cm⁻¹: 3260, 1680, 1430, 1325, 1155.
MS (m/z): 449 (M⁺).

Preparation Example 45

6-[2-[(4-Chlorophenyl)sulfonylaminomethyl]indan-5-yl]-3-oxo-2,3,4,5-tetrahydropyridazine 4-[2-[(4-Chlorophenyl)sulfonylaminomethyl]indan-5-yl]-4-oxobutanoic acid (1.730 g) obtained in Preparation Example 40 was suspended in acetic acid (12 ml), and hydrazine monohydrate (332 mg) was added to the suspension, followed by reflux. After 3.5 hours, acetic acid was distilled off under reduced pressure, and a saturated aqueous solution of sodium bicarbonate was added to the resultant residue. A crystal formed was collected by filtration. This crystal was dried and then recrystallized from acetic acid to obtain 1.331 g of a colorless crystal. Yield: 78%.

Melting point: 193°–194° C.
IR (KBr) cm⁻¹: 3250, 1685, 1315, 1150.
MS (m/z): 417 (M⁺).

Preparation Example 46

5-[2-[(4-Chlorophenyl)sulfonylaminomethyl]indan-5-yl]-3-oxo-2,3,4-trihydropyrazole
Step 1: Ethyl 3-[2-[(4-Chlorophenyl)sulfonylaminomethyl]indan- 5-yl]-3-oxopropionate The compound was obtained in the same manner as in Preparation Example 40. Yield: 70%.
Melting point: 78°–79° C. (ethyl acetate-isopropyl ether).
IR (KBr) cm⁻¹: 3240, 2920, 1730, 1675, 1150.
MS (m/z): 435 (M⁺).
Step 2: 5-[2-[(4-Chlorophenyl)sulfonylaminomethyl]indan-5-yl]-3-oxo-2,3,4-trihydropyrazole The compound was obtained in the same manner as in Preparation Example 45. Yield: 72%.
Melting point: 274°–275° C. (acetic acid).
IR (KBr) cm⁻¹: 3250, 1700, 1600, 1150.
MS (m/z): 403 (M⁺).

Preparation Example 47

3-[2-[(4-Chlorophenyl)sulfonylaminomethyl]indan-5-yl]-3-hydroxypropionic Acid
Step 1: Ethyl 3-[2-[(4-Chlorophenyl)sulfonylaminomethyl]indan-5-yl]-3-hydroxypropionate Dissolved in 60 ml of methanol were 4.46 g of ethyl 3-[2-[(4-chlorophenyl)sulfonylaminomethyl]indan-5-yl]-3-oxopropionate obtained in the step 1 of Preparation Example 46. While chilling with ice water, 193 mg of sodium borohydride were added to the solution. After the mixture was stirred for 2 hours at the same temperature, the solvent was distilled off under reduced pressure. After the residue was added with ethyl acetate, washed with water and dried, the solvent was distilled off under reduced pressure. The residue was recrystallized from a mixed solvent of ethyl acetate and isopropyl ether to obtain 4.37 g of a colorless crystal. Yield: 99%.
Melting point: 108°–111° C.
IR (KBr) cm⁻¹: 3260, 1725, 1325, 1155.
MS (m/z): 437 (M⁺).
Step 2: 3-[2-[(4-Chlorophenyl)sulfonylaminomethyl]indan-5-yl]-3-hydroxypropionic Acid The compound was obtained in the same manner as in the step 4 of Preparation Example 1. Yield: 89%.
Melting point: 173°–174° C. (ethyl acetate).
IR (KBr) cm⁻¹: 3260, 1705, 1325, 1155.
MS (m/z): 409 (M⁺).

Preparation Example 48

4-[2-[(4-Chlorophenyl)sulfonylaminomethyl]indan-5-yl]butanoic Acid
Step 1: Ethyl 4-[2-[(4-chlorophenyl)sulfonylaminomethyl]indan-5-yl]-4-oxobutyrate The compound was obtained in the same manner as in Preparation Example 40. Yield: 84%.
Melting point: 86°–87° C. (ethyl acetate-isopropyl ether).
IR (KBr) cm⁻¹: 3240, 1725, 1665, 1160.
MS (m/z): 449 (M⁺).
Step 2: Ethyl 4-[2-[(4-chlorophenyl)sulfonylaminomethyl]indan-5-yl]butyrate Dissolved in 10 ml of trifluoroacetic acid were 6.75 g of ethyl 4-[2-[(4-chlorophenyl)sulfonylaminomethyl]indan-5-yl]-4-oxobutyrate, and 5.4 ml of triethylsilane were added to the solution. The mixture was stirred overnight at room temperature. Water was added to the liquid reaction mixture, and the product formed was extracted with ethyl acetate. After the extract was washed successively with water, a saturated aqueous solution of sodium bicarbonate and saturated saline and dried, the solvent was distilled off under reduced pressure. The resultant residue was recrystallized from a mixed solvent of ethyl acetate and hexane to obtain 5.83 g of a colorless crystal. Yield: 89%.
Melting point: 70°–71° C.
IR (KBr) cm⁻¹: 3260, 1735, 1155.
MS (m/z): 435 (M⁺).

The following compounds of Preparation Examples 49–52 were obtained in accordance with the preparation process used in Preparation Example 48.

Preparation Example 49

5-[2-[(4-Chlorophenyl)sulfonylaminomethyl]indan-5-yl]pentanoic Acid

Melting point: 164°–165° C. (ethanol).
IR (KBr) cm⁻¹: 3260, 1700, 1155.

MS (m/z): 421 (M⁺).

Preparation Example 50

4-[2-[(4-Methoxyphenyl)sulfonylaminomethyl]indan-5-yl]butanoic Acid

Melting point: 114°–115° C. (aqueous ethanol).

IR (KBr) cm$^{-1}$: 3300, 1700, 1155.

MS (m/z): 403 (M⁺).

Preparation Example 51

6-[2-[(4-Chlorophenyl)sulfonylaminomethyl]indan-5-yl]hexanoic Acid

Melting point: 152°–153° C. (aqueous ethanol).

IR (KBr) cm$^{-1}$: 3250, 1700, 1435, 1325, 1155.

MS (m/z): 435 (M⁺).

Preparation Example 52

4-[2-[(2-Naphtylsulfonylaminomethyl)indan-5-yl]butanoic Acid

Melting point: 165°–167° C. (aqueous ethanol).

IR (KBr) cm$^{-1}$: 3255, 1695, 1155.

MS (m/z): 423 (M⁺).

The chemical structures of the compounds obtained in Preparation Examples 1–52 described above are shown in Tables 1–6:

TABLE 1

R²—Y—[indane]—(CH$_2$)$_n$—NHSO$_2$R¹

| Compound | R² | Y | n | R¹ |
|---|---|---|---|---|
| Prepn Ex. 1 | HOOC | CH$_2$ | 1 | phenyl |
| Prepn Ex. 2 | HOOC | CH$_2$ | 1 | 4-methylphenyl |
| Prepn Ex. 3 | HOOC | CH$_2$ | 1 | 2,3-dimethoxyphenyl |
| Prepn Ex. 4 | HOOC | CH$_2$ | 1 | —CH=CH—phenyl |
| Prepn Ex. 5 | HOOC | CH$_2$ | 1 | —CH$_2$—phenyl |

TABLE 1-continued

R²—Y—[indane]—(CH$_2$)$_n$—NHSO$_2$R¹

| Compound | R² | Y | n | R¹ |
|---|---|---|---|---|
| Prepn Ex. 6 | HOOC | CH$_2$ | 1 | 1-naphthyl |
| Prepn Ex. 7 | HOOC | CH$_2$ | 1 | 2-naphthyl |
| Prepn Ex. 8 | HOOC | CH$_2$ | 1 | 2-thienyl |
| Prepn Ex. 9 | HOOC | CH$_2$ | 1 | 5-(phenylsulfonyl)-2-thienyl |

TABLE 2

R²—Y—[indane]—(CH$_2$)$_n$—NHSO$_2$R¹

| Compound | R² | Y | n | R¹ |
|---|---|---|---|---|
| Prepn Ex. 10 | HOOC | CH$_2$ | 1 | 4-CF$_2$-phenyl |
| Prepn Ex. 11 | HOOC | CH$_2$ | 1 | 2,4-dichlorophenyl |
| Prepn Ex. 12 | HOOC | CH$_2$ | 1 | 4-OCH$_3$-phenyl |
| Prepn Ex. 13 | HOOC | CH$_2$ | 1 | 4-F-phenyl |
| Prepn Ex. 14 | HOOC | CH$_2$ | 1 | 4-Br-phenyl |
| Prepn Ex. 15 | HOOC | CH$_2$ | 1 | 2,3-dichlorophenyl |

TABLE 2-continued structure: R²—Y—[indene]—(CH₂)ₙ—NHSO₂R¹

| Compound | R² | Y | n | R¹ |
|---|---|---|---|---|
| Prepn Ex. 16 | HOOC | CH₂ | 1 | —C₆H₄—C₂H₅ |
| Prepn Ex. 17 | HOOC | CH₂ | 1 | —C₆H₄—C(CH₃)₃ |
| Prepn Ex. 18 | HOOC | CH₂ | 1 | —C₆H₄—C₈H₁₇ |

TABLE 3 structure: R²—Y—[indene]—(CH₂)ₙ—NHSO₂R¹

| Compound | R² | Y | n | R¹ |
|---|---|---|---|---|
| Prepn Ex. 19 | HOOC | CH₂ | 1 | —C₆H₄—OCF₃ |
| Prepn Ex. 20 | HOOC | CH₂ | 1 | —C₆H₄—OC₄H₉ |
| Prepn Ex. 21 | HOOC | CH₂ | 1 | —C₆H₄—CN |
| Prepn Ex. 22 | HOOC | CH₂ | 1 | —C₆H₄—NO₂ |
| Prepn Ex. 23 | HOOC | CH₂ | 1 | —C₆H₄—NH₂ |
| Prepn Ex. 24 | HOOC | CH₂ | 1 | —C₆H₄—Cl |
| Prepn Ex. 25 | HOOC | CH₂ | 2 | —C₆H₅ |
| Prepn Ex. 26 | HOOC | CH₂ | 2 | —C₆H₄—Cl |

TABLE 3-continued

| Compound | R² | Y | n | R¹ |
|---|---|---|---|---|
| Prepn Ex. 27 | HOOC | CH₂ | 3 | —C₆H₄—Cl |
| Prepn Ex. 28 | HOOC | CH₂ | 4 | —C₆H₄—Cl |

TABLE 4 structure: R²—Y—[indene]—(CH₂)ₙ—NHSO₂R¹

| Compound | R² | Y | n | R¹ |
|---|---|---|---|---|
| Prepn Ex. 29 | HOOC | CH₂O | 1 | —C₆H₅ |
| Prepn Ex. 30 | HOOC | CH₂O | 1 | —C₆H₄—Cl |
| Prepn Ex. 31 | HOOC | CH₂O | 1 | —C₆H₄—OCH₃ |
| Prepn Ex. 32 | HOOC | CH₂O | 2 | —C₆H₄—Cl |
| Prepn Ex. 33 | HOOC | — | 1 | —C₆H₄—Cl |
| Prepn Ex. 34 | HOOC | — | 2 | —C₆H₄—Cl |
| Prepn Ex. 35 | HOOC | — | 3 | —C₆H₄—Cl |
| Prepn Ex. 36 | HOOC | — | 4 | —C₆H₄—Cl |
| Prepn Ex. 37 | HOOC | CH=CH | 1 | —C₆H₄—Cl |

TABLE 4-continued $$R^2-Y-\text{[indene]}-(CH_2)_n-NHSO_2R^1$$

| Compound | $R^2$ | Y | n | $R^1$ |
|---|---|---|---|---|
| Prepn Ex. 38 | HOOC | $(CH_2)_2$ | 1 | 4-Cl-C$_6$H$_4$ |
| Prepn Ex. 39 | HOOC | $(CH_2)_2$ | 1 | 4-OCH$_3$-C$_6$H$_4$ |

TABLE 5

$$R^2-Y-\text{[indene]}-(CH_2)_n-NHSO_2R^1$$

| Compound | $R^2$ | Y | n | $R^1$ |
|---|---|---|---|---|
| Prepn Ex. 40 | HOOC | $(CH_2)_2CO$ | 1 | 4-Cl-C$_6$H$_4$ |
| Prepn Ex. 41 | HOOC | $(CH_2)_2CO$ | 2 | 4-Cl-C$_6$H$_4$ |
| Prepn Ex. 42 | HOOC | $(CH_2)_2CO$ | 1 | 4-OCH$_3$-C$_6$H$_4$ |
| Prepn Ex. 43 | HOOC | $(CH_2)_3CO$ | 1 | 4-Cl-C$_6$H$_4$ |
| Prepn Ex. 44 | HOOC | $(CH_2)_4CO$ | 1 | 4-Cl-C$_6$H$_4$ |
| Prepn Ex. 45 | pyridazinone-type | — | 1 | 4-Cl-C$_6$H$_4$ |
| Prepn Ex. 46 | pyridazinone-type | — | 1 | 4-Cl-C$_6$H$_4$ |
| Prepn Ex. 47 | HOOC | $CH_2(OH)CH$ | 1 | 4-Cl-C$_6$H$_4$ |

TABLE 5-continued

R²—Y—[indene]—(CH₂)ₙ—NHSO₂R¹

| Compound | R² | Y | n | R¹ |
|---|---|---|---|---|
| Prepn Ex. 48 | HOOC | (CH₂)₃ | 1 | —C₆H₄—Cl |

TABLE 6

R²—Y—[indene]—(CH₂)ₙ—NHSO₂R¹

| Compound | R² | Y | n | R¹ |
|---|---|---|---|---|
| Prepn Ex. 49 | HOOC | (CH₂)₄ | 1 | —C₆H₄—Cl |
| Prepn Ex. 50 | HOOC | (CH₂)₃ | 1 | —C₆H₄—OCH₃ |
| Prepn Ex. 51 | HOOC | (CH₂)₅ | 1 | —C₆H₄—Cl |
| Prepn Ex. 52 | HOOC | (CH₂)₃ | 1 | —naphthyl |

Test Example
Effect on Reduction of Serum Lipids

The sodium salt of each of compounds to be tested was suspended in a 0.5% methyl cellulose solution, and the suspension was orally administered to a group consisting of 5 male F344 rats (Charles River Co.) aged 6 weeks repeatedly for 2 weeks once a day. During this period, feed CRF-1 (Oriental Yeast Co., Ltd.) and drinking water (filtered and sterilized tap water) were freely ingested.

At 2 hours after the final administration, amounts of triglycerides and total cholesterol in a serum obtained from blood collected from an aorta abdominalis of each rat were determined by means of an automatic serum analyzer (IMPACT400E, GILFORD).

Incidentally, the blood collection was conducted at 2 hours after the final administration, and centrifugation after the blood samples was performed within 90 minutes after the blood collection. The determination was conducted after the serum was refrigerated and conserved.

On the basis of the results of this experiment, percent reduction of the total cholesterol value in the serum and percent reduction of the triglyceride value in the serum were determined in accordance with the following first and second equations, respectively. The results are as shown in Table 7.

First equation:
Percent reduction of the total cholesterol value in serum =

$$\left[1 - \frac{\text{Average amount of total cholesterol in serum of compound}}{\text{Average amount of total cholesterol in serum of control group}}\right] \times 100$$

*: Average amount of total cholesterol in serum of control group: 53–62 mg/dl

Second equation:
Percent reduction of the triglyceride value in serum =

$$\left[1 - \frac{\text{Average amount of triglycerides in serum of compound}}{\text{Average amount of triglyceride in serum of control group}}\right] \times 100$$

*: Average amount of triglycerides in serum of control group: 58–81 mg/dl.

TABLE 7

| Compound | Amount administered (mg/kg) | *Percent reduction of TC (%) | **Percent reduction of TG (%) |
|---|---|---|---|
| Prepn Ex. 24 | 100 | 24 | 41 |
| Prepn Ex. 33 | 100 | 30 | 61 |
| Prepn Ex. 35 | 100 | 0 | 22 |

*: Percent reduction of TC = Percent reduction of the amount of total cholesterol in serum.
**: Percent reduction of TG = Percent reduction of the amount of triglycerides in serum.

Toxicity Test

ICR mice (Charles River Co.) aged 4–5 weeks were used at a proportion of 10 mice per group. Each of the compounds prepared in Preparation Examples 1, 24, 25, 30, 33, 34 and 40 was suspended in 10% gum arabic. There after, the suspension was orally administered to a group of the mice in a dose of 300 mg/kg to observe the mice over 7 days. As a result, no lethal case was observed as to the compounds tested under the above-described conditions.

Formulation Example 1

| Compound of Preparation Example 1 | 20 g |
|---|---|
| Lactose | 315 g |
| Corn starch | 125 g |
| Crystalline cellulose | 25 g |

The components of the above composition were intimately mixed, and 200 ml of a 7.5% aqueous solution of hydroxypropyl cellulose were added thereto. The mixture was extruded into granules through an extrusion granulator making use of a screen having openings of 0.5 mm in diameter. The granules were immediately rounded by a Marumelyzer and then dried to obtain a granular preparation.

Formulation Example 2

| Compound of Preparation Example 24 | 20 g |
| Lactose | 100 g |
| Corn starch | 36 g |
| Crystalline cellulose | 30 g |
| Calcium carboxymethyl cellulose | 10 g |
| Magnesium stearate | 4 g. |

The components of the above composition were intimately mixed, and the mixture was tableted by a single table machine with a pestle 7.5 mm in diameter, thereby obtaining a tablet preparation having a weight of 200 mg/tablet.

Formulation Example 3

| Compound of Preparation Example 40 | 40 g |
| Lactose | 232 g |
| Corn starch | 108 g |
| Polyvinyl pyrrolidone | 20 g. |

The components of the above composition were intimately mixed, and 180 ml of 70% (v/v) isopropyl alcohol were added thereto. The mixture was extruded into granules through an extrusion granulator making use of a screen having openings of 0.8 mm in diameter. The granules were immediately rounded by a Marumelyzer and then dried to obtain a granular preparation. The granular preparation was charged into No. 2 hard gelatin capsules, thereby obtaining a capsule preparation having a content of 240 mg/capsule.

INDUSTRIAL APPLICABILITY

Since the remedies for hyperlipidemia according to the present invention have an excellent effect for reducing lipids in blood and are also high in safety, they are useful for the treatment for and prevention of hyperlipidemia, or diseases caused by the hyperlipidemia, such as myocardial infarction, cerebral infarction, occlusion of peripheral artery and arteriosclerosis.

We claim:

1. A method for treating hyperlipidemia, which comprises administering an effective amount of an indane derivative represented by the general formula (1):

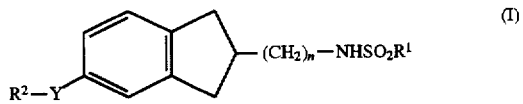

wherein $R^1$ means an alkyl group having 1-12 carbon atoms, a benzyl group, a styryl group, a naphthyl group, a phenyl group which may be substituted, or a thienyl group which may be substituted, $R^2$ denotes a carboxyl group, an alkoxycarbonyl group having 1-4 carbon atoms,

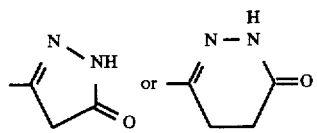

Y is a group represented by —$(CH_2)_p$— (p stands for an integer of 0–5), a group represented by —CO—$(CH_2)_q$— or —CH(OH)—$(CH_2)_q$— (q stands for an integer of 1–4, and – means bonding to $R^2$), an oxymethylene group, or a vinylene group, and n stands for an integer of 1–4 or the pharmaceutically acceptable salt thereof to a patient having hyperlipidemia.

2. The method according to claim 1, wherein the indane derivative is administered with a pharmaceutically acceptable carrier.

3. The method according to claim 1, wherein the indane derivative is [2-(phenylsulfonylaminomethyl)indan-5-yl] acetic acid.

4. The method according to claim 1, wherein the indane derivative is [2-[(4-chlorophenyl)sulfonylaminomethyl] indan-5-yl]acetic acid.

5. The method according to claim 1, wherein the indane derivative is 4-[2-[(4-chlorophenyl)sulfonylaminomethyl] indan-5-yl]-4-oxobutanoic acid.

* * * * *